(12) United States Patent
Hull et al.

(10) Patent No.: US 10,631,913 B2
(45) Date of Patent: Apr. 28, 2020

(54) FILTER CIRCUIT FOR ELECTROPHYSIOLOGY SYSTEM

(71) Applicant: St. Jude Medical, Cardiology Division, Inc., St. Paul, MN (US)

(72) Inventors: Larry J. Hull, Scandia, MN (US); Timothy G. Curran, Ramsey, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 427 days.

(21) Appl. No.: 14/971,497

(22) Filed: Dec. 16, 2015

(65) Prior Publication Data

US 2016/0184004 A1 Jun. 30, 2016

Related U.S. Application Data

(60) Provisional application No. 62/098,848, filed on Dec. 31, 2014.

(51) Int. Cl.
*A61B 18/12* (2006.01)
*A61B 5/042* (2006.01)
(Continued)

(52) U.S. Cl.
CPC ........ *A61B 18/1233* (2013.01); *A61B 5/0422* (2013.01); *A61B 5/0428* (2013.01);
(Continued)

(58) Field of Classification Search
CPC ........... A61B 2018/00357; A61B 2018/00577; A61B 2018/00839; A61B 2018/1293; A61B 2018/167; A61B 34/73; A61B 18/1233; A61B 18/1492; A61B 2034/2046; A61B 2090/065; A61B 2090/374; A61B 2090/376; A61B 2218/002; A61B 5/0422; A61B 5/0428; A61B 5/0538; A61B 5/6852; A61N 1/36017; A61N 1/3625
See application file for complete search history.

(56) References Cited

U.S. PATENT DOCUMENTS 5,300,068 A 4/1994 Rosar et al.
5,569,245 A * 10/1996 Guglielmi ........ A61B 17/12022
606/32
(Continued)

FOREIGN PATENT DOCUMENTS

CN 101601890 A 12/2009
CN 202136417 U 2/2012
(Continued)

*Primary Examiner* — Daniel W Fowler
(74) *Attorney, Agent, or Firm* — Dykema Gossett PLLC

(57) ABSTRACT

An ablation generator may include an input port for receiving a monitoring signal respective of tissue of the patient and an output port for providing the monitoring signal another device. A filtering circuit may be disposed between the input port and the output port, the filtering circuit configured to present a high impedance at one or more frequencies at or near which a mapping and navigation system associated with the ablation generator transmits a signal. The filtering circuit may additionally or alternatively be provided in a monitoring system or another component in an electrophysiology system.

3 Claims, 8 Drawing Sheets

(51) Int. Cl.
  *A61B 5/0428* (2006.01)
  *A61N 1/36* (2006.01)
  *A61N 1/362* (2006.01)
  *A61B 5/00* (2006.01)
  *A61B 18/00* (2006.01)
  *A61B 5/053* (2006.01)
  *A61B 18/14* (2006.01)
  *A61B 34/20* (2016.01)
  *A61B 90/00* (2016.01)
  *A61B 18/16* (2006.01)
  *A61B 34/00* (2016.01)
  *H03H 7/01* (2006.01)
  *H03H 7/06* (2006.01)

(52) U.S. Cl.
  CPC ....... *A61N 1/36017* (2013.01); *A61N 1/3625* (2013.01); *A61B 5/0538* (2013.01); *A61B 5/6852* (2013.01); *A61B 18/1492* (2013.01); *A61B 34/73* (2016.02); *A61B 2018/00357* (2013.01); *A61B 2018/00577* (2013.01); *A61B 2018/00839* (2013.01); *A61B 2018/1293* (2013.01); *A61B 2018/167* (2013.01); *A61B 2034/2046* (2016.02); *A61B 2090/065* (2016.02); *A61B 2090/374* (2016.02); *A61B 2090/376* (2016.02); *A61B 2218/002* (2013.01); *H03H 7/06* (2013.01); *H03H 7/1766* (2013.01)

(56) References Cited

U.S. PATENT DOCUMENTS

| | | | | |
|---|---|---|---|---|
| 5,643,255 | A * | 7/1997 | Organ | A61B 18/1492 606/34 |
| 6,113,595 | A | 9/2000 | Muntermann | |
| 6,233,476 | B1 | 5/2001 | Strommer | |
| 6,498,944 | B1 | 12/2002 | Ben-Haim et al. | |
| 6,690,963 | B2 | 2/2004 | Ben-Haim et al. | |
| 6,788,967 | B2 | 9/2004 | Ben-Haim et al. | |
| 7,197,354 | B2 | 3/2007 | Sobe | |
| 7,263,397 | B2 | 8/2007 | Hauck et al. | |
| 7,386,339 | B2 | 6/2008 | Strommer et al. | |
| 7,536,218 | B2 | 5/2009 | Govari et al. | |
| 7,885,707 | B2 | 2/2011 | Hauck | |
| 8,403,925 | B2 | 3/2013 | Miller et al. | |
| 2005/0187482 | A1 | 8/2005 | O'Brien et al. | |
| 2007/0060833 | A1 | 3/2007 | Hauck | |
| 2008/0140066 | A1 * | 6/2008 | Davison | A61B 18/1402 606/37 |
| 2009/0099440 | A1 * | 4/2009 | Viohl | A61B 5/042 600/373 |
| 2009/0275827 | A1 | 11/2009 | Aiken et al. | |
| 2009/0306641 | A1 | 12/2009 | Govari et al. | |
| 2010/0049031 | A1 * | 2/2010 | Fruland | A61B 18/1492 600/411 |
| 2010/0168557 | A1 | 7/2010 | Deno et al. | |
| 2010/0191238 | A1 * | 7/2010 | Kornerup | A61B 18/1206 606/47 |
| 2010/0286686 | A1 * | 11/2010 | Hancock | A61B 18/18 606/33 |
| 2011/0118727 | A1 | 5/2011 | Fish et al. | |
| 2012/0116386 | A1 * | 5/2012 | Govari | A61B 18/1206 606/41 |
| 2012/0203169 | A1 | 8/2012 | Tegg | |
| 2013/0066193 | A1 | 3/2013 | Olson et al. | |
| 2014/0358038 | A1 | 12/2014 | Byrd et al. | |

FOREIGN PATENT DOCUMENTS

| | | |
|---|---|---|
| CN | 102525642 A | 7/2012 |
| CN | 104023621 A | 9/2014 |
| CN | 104185450 A | 12/2014 |
| EP | 2130507 | 12/2009 |
| WO | 2004/018037 A1 | 3/2004 |

* cited by examiner

FILTER CIRCUIT FOR ELECTROPHYSIOLOGY SYSTEM

CROSS-REFERENCE TO RELATED APPLICATIONS

This application claims the benefit of U.S. provisional application No. 62/098,848, filed Dec. 31, 2014, which is hereby incorporated by reference as though fully set forth herein.

BACKGROUND a. Technical Field

The instant disclosure relates to a filtering circuit for use in an electrophysiology (EP) system, including an EP system having an ablation generator, an EP recorder, and/or a mapping and navigation system.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site such as, for example, a site within the patient's heart. The catheter typically carries one or more electrodes, which may be used for ablation, diagnosis, and the like.

Catheters may be used in a system or laboratory with numerous electrical systems and components. For example, an ablation system, stimulation system, electrogram system, and mapping and navigation system may all be used during a single procedure, and may all transmit, collect, and/or monitor electrical signals of different respective frequencies, currents, and voltages.

The foregoing discussion is intended only to illustrate the present field and should not be taken as a disavowal of claim scope.

BRIEF SUMMARY

An embodiment of an ablation generator may include a circuit for generating an RF ablation signal having a frequency appropriate for performing an ablation procedure on tissue of a patient, an input port for receiving a monitoring signal respective of the tissue of the patient, and an output port for providing the monitoring signal to another device. The ablation generator may further include a filtering circuit disposed between the input port and the output port. The filtering circuit may be configured to present a very high impedance at one or more frequencies at or near which a mapping and navigation system associated with the ablation generator transmits a signal, at or near a frequency of the RF ablation signal, and/or at or near frequencies of one or more harmonics of the RF ablation signal.

An embodiment of an electrical circuit may include an input node for receiving a monitoring signal respective of tissue of a patient, an output node for providing the monitoring signal to a monitoring system, and a signal path from the input node to the output node. The electrical circuit may further include a filtering circuit disposed in the signal path. The filtering circuit may include a plurality of LC traps, each LC trap comprising an inductor in parallel with a capacitor, the plurality of LC traps being placed in series. A first of the LC traps may be tuned to a peak frequency of between six kilohertz and eight kilohertz. A second of the LC traps may be tuned to a peak frequency of between 450 kilohertz and 500 kilohertz. A third of the LC traps may be tuned to a peak frequency of between one and two megahertz.

An exemplary system may include an electrophysiology recording system and an ablation generator that is configured to output an RF ablation signal for a medical device to perform an ablation procedure on tissue of a patient, configured to receive an electrogram respective of tissue of the patient, and to transmit the electrogram over a signal pathway for the electrophysiology recording system. The system may further include a filtering circuit, disposed in the signal pathway, comprising a plurality of LC traps, each of the LC traps comprising an inductor in parallel with a capacitor, the plurality of LC traps being placed in series.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment.

Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

Figure 1:
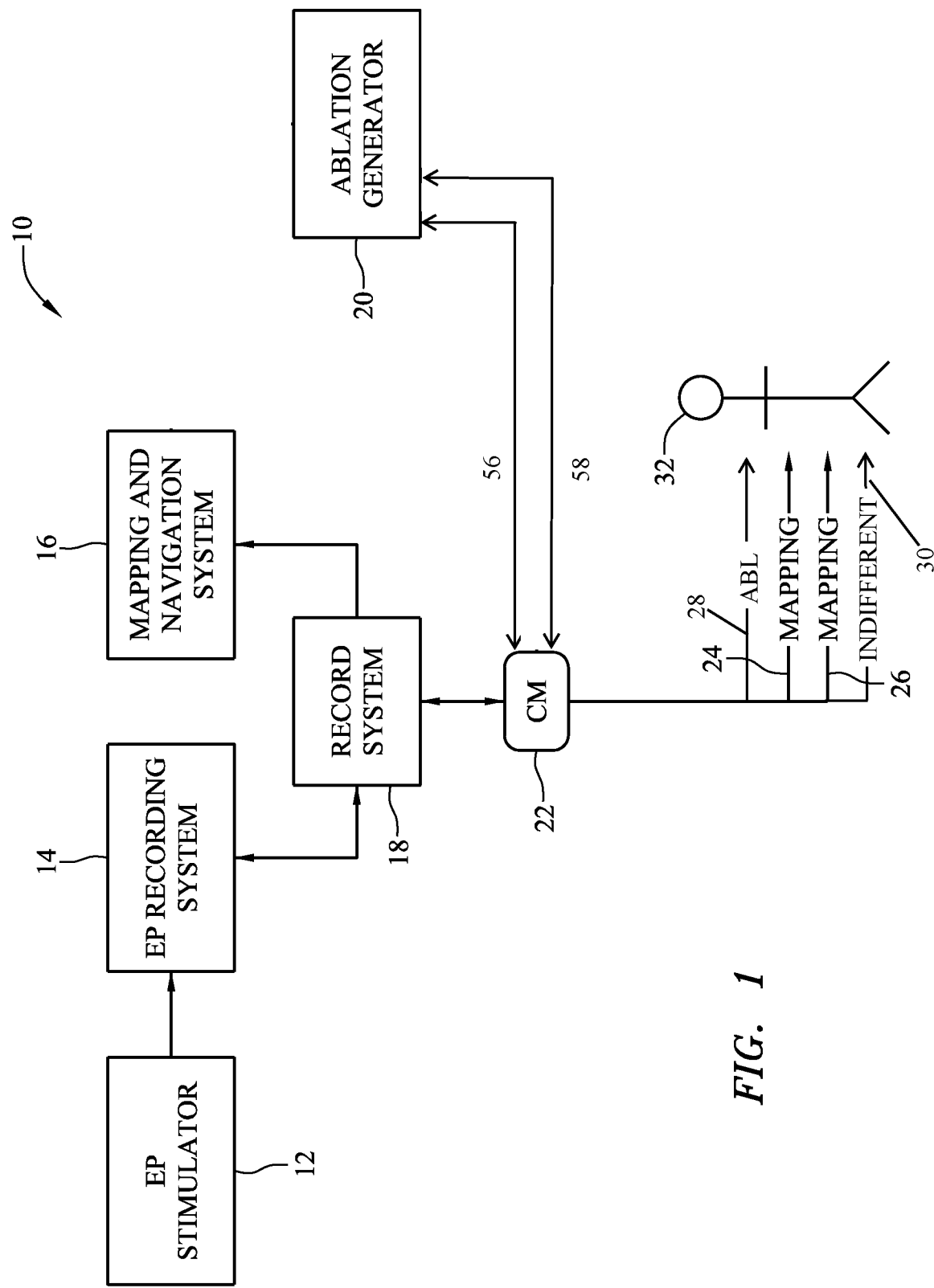
FIG. 1 is a diagrammatic view of an exemplary embodiment of an electrophysiology system.

Referring now to the figures, in which like reference numerals indicate the same or similar elements in the various views, FIG. 1 is a diagrammatic view of an exemplary embodiment of an electrophysiology (EP) system 10. The system 10 may include an EP stimulator 12, an EP recording system 14, a mapping and navigation system 16, a record and data consolidation system 18 (shown as "record system" 18 in FIG. 1), an ablation generator 20, a tissue contact and coupling monitor 22 (abbreviated "CM" 22 in FIG. 1), and a number of medical devices for performing a diagnostic and/or therapeutic procedure on a patient 32. For example, in an exemplary embodiment, three elongate medical devices may be provided: a first mapping and diagnosis catheter 24, a second mapping and diagnosis catheter 26, and an ablation catheter 28. An RF indifferent patch 30, for returning an RF ablation signal driven through the ablation catheter 28, may also be provided in the system.

The instant disclosure provides, among other things, a filtering circuit that may find use with an EP system combining ablation, electrical impedance-based mapping and navigation, and/or electrogram recording capabilities (e.g., the EP system 10 of FIG. 1) or another system or laboratory. Such a filtering circuit may be provided in one or more of the systems and devices illustrated in FIG. 1 or in separate hardware. The systems and devices illustrated in FIG. 1 will first be briefly described with reference to FIGS. 1-3. An exemplary filtering circuit and the operation of the filtering circuit will then be described with reference to FIGS. 4-9. Finally, exemplary pacing functionality that may be performed in conjunction with an ablation procedure (e.g., in a system including a filtering circuit according to the present disclosure) will be described with reference to FIGS. 10 and 11, and an exemplary mapping and navigation system will be described with reference to FIG. 12.

Components of the EP System. The electrophysiology stimulator 12 may include one or more devices for providing and controlling electrical stimulation of an organ of the patient. For example, the electrophysiology stimulator 12 may include an electronic control unit (ECU) for controlling the provision of electrical stimulation pulses (also referred to herein as pacing signals) intended for a patient's heart and a circuit for producing such pulses. Such pulses may be provided, for example, during an electrophysiology study of the heart through, for example, one or more of the mapping catheters 24, 26 or the ablation catheter 28. In an exemplary embodiment, the EP stimulator may comprise an EP-4™ Cardiac Stimulator commercially available from St. Jude Medical, Inc. of St. Paul, Minn.

The EP recording system 14 may include one or more devices configured to obtain, record, and/or display an electrogram respective of the patient 32. For example, the EP recording system 14 may include or be electrically coupled with a set of electrocardiogram (ECG) patches and may record and display an electrocardiogram or other electrogram for clinician review. The EP recording system 14 may additionally or alternatively collect, record, and/or display ECG or other electrogram data measured with or by the ablation generator 20, the mapping and navigation system 16, and/or another component of the EP system 10. In an embodiment, the EP recording system may comprise the WorkMate™ Claris™ Recording System commercially available from St. Jude Medical, Inc. of St. Paul, Minn.

The mapping and navigation system 16 may be provided for various functions including, but not limited to, determining the location (i.e., position and orientation) of an elongate medical device (such as one or more of the mapping catheters 24, 26 and the ablation catheter 28) within the body of the patient 32, mapping the anatomy of the patient 32, etc. The mapping and navigation system 16 may comprise an electrical impedance-based system, such as, for example, an EnSite™ Velocity™ cardiac electro-anatomic mapping system running a version of EnSite™ NavX™ navigation and visualization technology software commercially available from St. Jude Medical, Inc., of St. Paul, Minn. and as also seen generally by reference to U.S. Pat. Nos. 7,263,397 and 7,885,707, both hereby incorporated by reference in their entireties. In other exemplary embodiments, the mapping and navigation system 16 may comprise systems other than electric impedance-based systems. For example, the mapping and navigation system 16 may comprise a magnetic field-based system such as the Carto™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another exemplary embodiment, the mapping and navigation system 16 may comprise a magnetic field-based system based on the MediGuide™ technology available from St. Jude Medical, Inc., and as generally shown with reference to one or more of U.S. Pat. Nos. 6,233,476; 7,197,354; and 7,386,339, the disclosures of which are hereby incorporated by reference in their entireties as though fully set forth herein. In yet another embodiment, the mapping and navigation system 16 may comprise a combination electrical impedance-based and magnetic field-based system, such as, for example and without limitation, the system described in pending U.S. patent application Ser. No. 13/231,284, or the Carto™ 3 system commercially available from Biosense Webster, and as generally shown with reference to U.S. Pat. No. 7,536,218, the disclosures of which are hereby incorporated by reference in their entireties as though set fully forth herein. In yet still other exemplary embodiments, the mapping and navigation system may comprise or be used in conjunction with other commonly available systems, such as, for example and without limitation, fluoroscopic, computed tomography (CT), and magnetic resonance imaging (MRI)-based systems.

An exemplary embodiment of an electrical impedance-based mapping and navigation system is illustrated in FIG. 12 and described in detail with reference to FIG. 12 at the end of this Detailed Description. Briefly, an electrical impedance-based mapping and navigation system may operate by driving electrical currents along several axes through the patient's body. For example, currents may be driven between pairs of cutaneous patch electrodes. The signals may have a frequency on the order of kilohertz (kHz), in an embodiment. For example, the signals may have a frequency between about six (6) kHz and about ten (10) kHz. Still further, for example, the signals may have a frequency of about eight (8) kHz, such as 8.138 kHz, in an embodiment. Electrodes within the patient's body may be used to detect the electrical signals, and the location of an electrode may be determined by assessing the detected signals.

The mapping and navigation system 16 may be further configured to collect EP and/or positioning data from the mapping catheters 24, 26. Based on such data, the mapping and navigation system 16 may be configured to, among other things, construct a model of patient tissue (e.g., of the heart), construct an EP map of patient tissue, etc.

With continued reference to FIG. 1, the record and data consolidation system 18 may include one or more devices configured to provide communication between the mapping and navigation system 16 and the EP recording system 14 to link data collection before, during and after a procedure. The record and data consolidation system 18 may be further configured to store, retrieve, display, and/or transmit patient data and other information, in an embodiment.

The record and data consolidation system 18 may provide a single system through which a clinician (e.g., a physician) may access data from either the EP recording system 14, the mapping and navigation system 16, and/or other systems that would otherwise be separate. For example, the record and data consolidation system 18 may be configured to provide the clinician with a single patient record including EP recording and charting (e.g., from the EP recording system 14) and maps and images of the patient's anatomy (e.g., from the mapping and navigation system 16). The record and data consolidation system 18 may comprise, in an embodiment, an EnSite™ Derexi™ module commercially available from St. Jude Medical, Inc. of St. Paul, Minn.

The tissue contact and coupling monitor 22 may be configured to perform one or more measurements, calculations, and output functions related to determining a contact or coupling state between a medical device and patient tissue, in an embodiment. The tissue contact and coupling monitor 22 may receive measurements respective of electrical characteristics of patient tissue from one or more electrodes included on the mapping catheters 24, 26 for example, and determine a coupling or contact state between one of the mapping catheters 24, 26 (e.g., an electrode disposed on one of the mapping catheters 24, 26) and the tissue based on the measurements. Such measurements and/or calculations may include, for example only, a complex impedance (i.e., reactance and resistance or impedance magnitude and phase angle), electrical coupling index (ECI), and/or other metric. Exemplary metrics and the use of such metrics for determining a contact or coupling state are described in greater detail in, for example, U.S. patent application publication no. 2009/0275827, which is hereby incorporated by reference in its entirety. Complex impedance, ECI, and similar metrics may also be used to assess the formation of lesions during or after an ablation procedure as described, for example, in U.S. patent application publication no. 2011/0118727, which is hereby incorporated by reference in its entirety.

The ablation generator 20 may be configured to provide an RF ablation signal for performing an ablation procedure (e.g., on a portion of the heart of the patient 32). Accordingly, the ablation generator 20 may be configured to drive an RF ablation signal through one or more electrodes on the ablation catheter 28, which signal may be returned through the RF indifferent patch 30. The ablation generator 20 may comprise or may include the functionality of, for example, the Ampere™ RF Ablation Generator or the IBI-1500T9-CP Cardiac Ablation Generator, both commercially available from St. Jude Medical, Inc. of St. Paul, Minn.

The ablation generator 20 may be further configured to collect signals respective of electrical activity of an organ of the patient 32 (i.e., electrogram signals), in an embodiment. For example, the ablation generator 20 may be configured to receive electrical signals collected with one or more electrodes on the ablation catheter 28. The ablation generator 20 may be further configured to provide such signals to one or more other components or systems within the EP system 10 such as, for example, to the tissue contact and coupling monitor 22. The EP system 10 may include a signal path between the ablation generator 20 and one or more other systems or devices in the EP system 10. For example, the EP system may include a signal path between the ablation generator 20 and the EP recording system 14, in an embodiment, for the EP recording system 14 to receive electrogram signals or data collected by, with, or through the ablation generator 20. This signal path may be referred to herein as the "electrogram signal path." The electrogram signal path may be direct or indirect, in embodiments. For example, as illustrated in FIG. 1, the electrogram signal path may go through the tissue contact and coupling monitor 22 and the record and data consolidation system 18. A signal path from the EP stimulator 12 to the ablation generator 20 may also be provided and may coincide, in part, with the electrogram signal path, in an embodiment.

The ablation generator 20 may be further configured to receive a pacing signal from, for example, the tissue contact and coupling monitor 22. The pacing signal may be originally generated, in an embodiment, by the EP stimulator 12, in an embodiment. The ablation generator 20 may be configured to provide the pacing signal through the ablation catheter 28. The pacing signal may be applied to tissue through, for example only, one or more electrodes of the ablation catheter 28.

One or more of the EP stimulator 12, the EP recording system 14, the mapping and navigation system 16, the record and data consolidation system 18, the ablation generator 20, and the tissue contact and coupling monitor 22 may include processing apparatus for performing the functions described herein. For example, one or more of the EP stimulator 12, the EP recording system 14, the mapping and navigation system 16, the record and data consolidation system 18, the ablation generator 20, and the tissue contact and coupling monitor 22 may include a respective ECU comprising a respective processor and a respective memory. The memory may store instructions that, when executed by the processor, cause the ECU to perform one or more of the functions described herein. Additional or alternative processing apparatus means may be provided, such as an application-specific integrated circuit (ASIC), field-programmable gate array (FPGA), or programmable logic device (PLD), for example only.

One or more the EP stimulator 12, the EP recording system 14, the mapping and navigation system 16, the record and data consolidation system 18, the ablation generator 20, and the tissue contact and coupling monitor 22 may further include a respective display and/or other input and output devices.

In an embodiment, one or more of the systems and devices illustrated separately in FIG. 1 may be included in a consolidated system or apparatus. For example, in an embodiment, the EP stimulator 12, EP recording system 14, and the record and data consolidation system 18 may be provided in a single system, product, or unit. For example, the EP stimulator 12, EP recording system 14, and the record and data consolidation system 18 may collectively comprise a WorkMate™ Claris™ Recording System commercially available from St. Jude Medical, Inc. of St. Paul, Minn.

Figure 2:
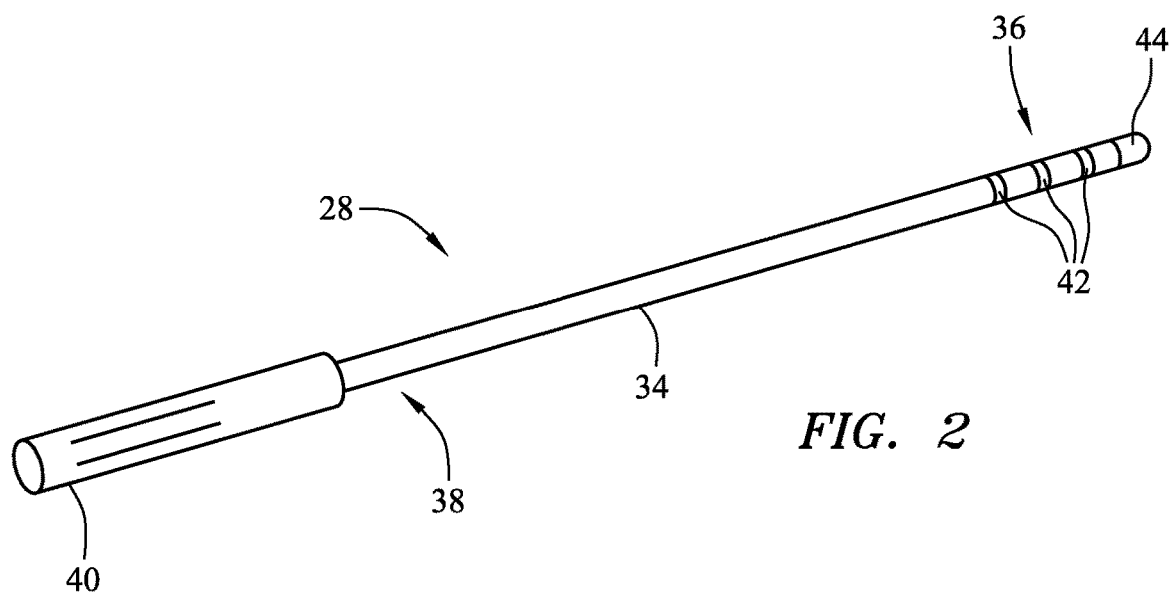
FIG. 2 is an isometric view of an exemplary embodiment of an ablation catheter.
Figure 3:
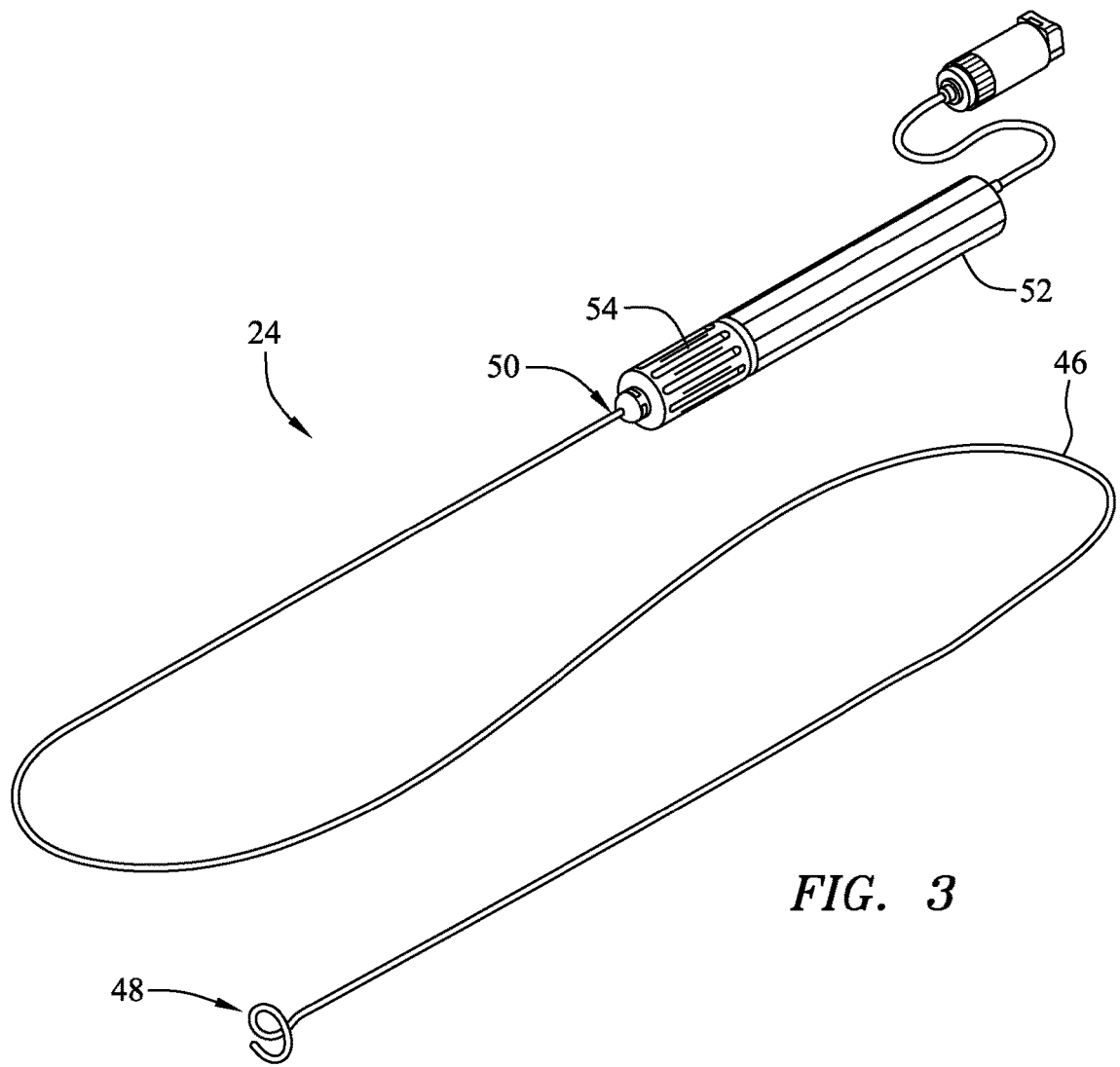
FIG. 3 is an isometric view of an exemplary embodiment of a mapping catheter.

Exemplary embodiments of the ablation catheter 28 and the first mapping catheter 24 are illustrated in FIGS. 2 and 3, respectively. Referring to FIG. 2, which is an isometric view of the ablation catheter 28, the ablation catheter 28 may comprise a shaft 34 having a distal end portion 36 and a proximal end portion 38. The ablation catheter 28 may be configured to be guided through and disposed in the body of a patient. Accordingly, the proximal end portion 38 may be coupled to a handle 40, which may include features to enable a physician to guide the distal end portion 36 to perform a diagnostic or therapeutic procedure such as, for example only, an ablation procedure on the heart of the patient. Accordingly, the handle 40 may include one or more manual manipulation mechanisms such as, for example, rotational mechanisms and/or longitudinal mechanisms, coupled to pull wires for deflecting the distal end portion 36 of the shaft 34. Exemplary embodiments of manipulation mechanisms, pull wires, and related hardware are described, for example only, in U.S. patent application publication no. 2012/0203169, hereby incorporated by reference in its entirety. The handle 40 may further include one or more electromechanical connectors for coupling to a mapping and navigation system, an ablation generator, and/or other external systems. The handle 40 may also include one or more fluid connectors for coupling to a source and/or destination of fluids such as, for example only, a gravity feed or fixed or variable-rate pump.

The distal end portion 36 of the shaft 34 may include a number of ring electrodes 42 and a tip electrode 44 for applying ablation energy to tissue, acquiring electrophysiology data from tissue, sensing positioning signals used to determine the position and orientation (P&O) of the shaft, and/or other purposes. The electrodes 42, 44 may be coupled to electrical wiring within the shaft 36, which wiring may extend to the handle 40 and to electromechanical connectors for coupling to external systems.

The distal end portion 36 of the shaft 34 may also include one or more fluid ports or manifolds for distributing or collecting fluids such as, for example only, irrigation fluid during an ablation procedure. The fluid ports may be fluidly coupled with one or more fluid lumens extending through the shaft 36 to the handle 40 and a fluid connector for coupling to external fluid sources and/or destinations.

FIG. 3 is an isometric view of an exemplary embodiment of the first mapping catheter 24, wherein the first mapping catheter 24 has a distal lariat portion (i.e., the illustrated embodiment of the first mapping catheter 24 is a spiral mapping catheter). The first mapping catheter 24 may comprise a shaft 46 having a distal end portion 48 and a proximal end portion 50. The first mapping catheter 24 may be configured to be guided through and disposed in the body of a patient. Accordingly, the proximal end portion 50 of the shaft 46 may be coupled to a handle 52, which may include features to enable a physician to guide the distal end portion to perform a diagnostic or therapeutic procedure such as, for example only, a mapping procedure on the heart of the patient. Accordingly, the handle 52 may include one or more manual manipulation mechanisms 54 such as, for example, rotational mechanisms and/or longitudinal mechanisms, coupled to pull wires for deflecting the distal end portion of the shaft. Exemplary embodiments of manipulation mechanisms, pull wires, and related hardware are described, for example only, in U.S. patent application publication no. 2012/0203169, referenced above. The handle 52 may further include one or more electromechanical connectors for coupling to a mapping and navigation system, an ablation generator, and/or other external systems. The handle 52 may also include one or more fluid connectors for coupling to a source and/or destination of fluids such as, for example only, a gravity feed or fixed or variable-rate pump.

The distal end portion 48 of the shaft may have a portion having a lariat shape. In an embodiment, the lariat shape may be formed by, for example, a shape memory wire disposed within the shaft. A tip electrode and a number of ring electrodes (similar to the tip and ring electrodes 44, 42 on the ablation catheter 28 and shown in FIG. 2) may be disposed on the distal end portion 48 of the shaft 46, in an embodiment. For example, a tip electrode and a plurality of ring electrodes may be disposed on the lariat portion of the shaft 46. In an embodiment, the distal end portion 48 may include nine (9) ring electrodes (i.e., a "decapolar" catheter having ten total electrodes) or nineteen (19) ring electrodes (i.e., a "duo-decapolar" catheter having twenty total electrodes). The electrodes may be coupled to electrical wiring within the shaft 46, which may extend to the handle 52 and to electromechanical connectors for coupling to external systems.

The catheter embodiments 24, 28 illustrated in FIGS. 2 and 3 are exemplary in nature only. Numerous types of catheters may find use in the EP system 10 of FIG. 1, as may numerous types of elongate medical devices, including catheters, introducers, guidewires, and the like. For example, the second mapping catheter 26 may be a coronary sinus catheter, in an embodiment, or other mapping catheter. Thus, embodiments including one or more elongate medical devices other than the catheters explicitly illustrated and described herein remain within the spirit and scope of the present disclosure.

Referring again to FIG. 1, the mapping catheters 24, 26 may be configured (e.g., through electrodes disposed on the respective shafts of the mapping catheters 24, 26) to collect electrical signals from the patient's body and to provide the electrical signals to the tissue contact and coupling monitor 22 for monitoring of contact and coupling between the electrodes and patient tissue. The electrical signals collected by the mapping catheters 24, 26 may also be provided to the mapping and navigation system 16 for, e.g., building a model and/or an EP map of the heart of the patient 32 or of a portion of the heart of the patient 32.

As noted above and in the various above-referenced patents and patent applications, a number of electrical signals may be transmitted and/or measured in and through the body of the patient 32 during a diagnostic and/or therapeutic procedure using the EP system 10 or components of the EP system 10. For example, during an ablation and monitoring procedure, various electrical signals may be transmitted by the components of the EP system 10, including positioning signals by the mapping and navigation system 16, ablation signals, and pacing signals. Furthermore, signals produced by the tissue of the patient 32, such as an ECG and/or localized electrical activity, may be monitored to, e.g., monitor tissue functionality to determine if a desired ablation lesion has been formed, to display for a clinician, etc. Accordingly, to maintain signal fidelity in the intended systems (i.e., positioning signal fidelity for the mapping and navigation system 16, electrogram signal fidelity for the EP recording system 14, etc.), one or more filtering circuits may be provided in the EP system 10 to minimize diversion or leakage of electrical currents from their intended paths.

In addition to unintended signal diversion or leakage, an issue in the electrical circuitry of the EP system 10 and other systems and laboratories may be properly protecting the various systems and devices from the signals emitted by the other devices and systems and/or filtering to be able to properly observe signals of a desired frequency. For example, electrogram signals (which may have a relatively low frequency and/or voltage) may be collected with the same electrodes that are used to drive ablation currents (which may be of a higher frequency and/or voltage). Furthermore, the current and/or voltage of the ablation signal may be higher than signals that the EP recording system 14 and/or other systems and devices are normally configured to receive. Accordingly, filtering the ablation signal from being returned through the electrogram signal path may be beneficial both for signal fidelity and for protecting equipment in the EP system.

The benefits of a filtering circuit listed above are exemplary in nature only. A filtering circuit according to the present disclosure may provide numerous benefits in addition to or instead of those expressly set forth herein, in embodiments.

Figure 4:
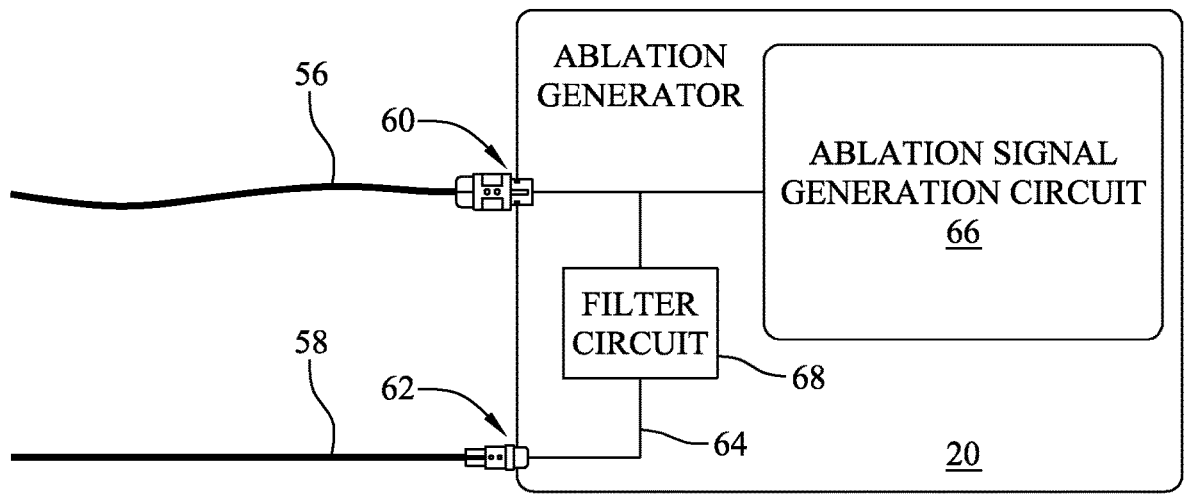
FIG. 4 is a diagrammatic view of a portion of the electrophysiology system of FIG. 1.

Filtering Circuit. FIG. 4 is a diagrammatic view of a portion of the EP system illustrated in FIG. 1. More specifically, FIG. 4 illustrates the ablation generator 20, an input/output (I/O) cable 56 for the ablation catheter, and an electrogram I/O cable 58.

The ablation catheter I/O cable 56 may be mechanically and electrically coupled to a first port 60 provided on the ablation generator 20. Ablation signals and/or other signals and data may be output to the ablation catheter through the ablation catheter I/O cable 56, and electrogram signals and/or other signals and data may be input to the ablation generator 20 through the ablation catheter I/O cable 56. Accordingly, the first port 60 may comprise or may be electrically coupled with an input node for electrogram signals.

The electrogram I/O cable 58 may be mechanically and electrically coupled to a second port 62 provided on the ablation generator. Electrogram signals and/or other signals or data may be output by the ablation generator 20 through the electrogram I/O cable 58, and pacing signals and/or other signals or data may be input to the ablation generator 20 through the electrogram I/O cable 58. Accordingly, the second port 62 may comprise or may be electrically coupled with an output node for electrogram signals and/or an input node for pacing signals.

As noted above, one or more electrodes on an ablation catheter may be used to collect electrogram signals, which signals may be provided to the ablation generator 20 from the ablation catheter through the ablation catheter I/O cable 56, and from the ablation generator 20 to one or more other systems or devices (such as the tissue contact and coupling monitor 22 or the EP recording system 14, for example—see FIG. 1). Accordingly, the ablation generator 20 may include a signal path 64 from the ablation catheter I/O cable 56 to the electrogram I/O cable 58. This signal path may be a portion of the electrogram signal path referenced above and below.

The ablation generator 20 may include, in an embodiment, an ablation signal generation circuit 66, a filtering circuit 68, and the above-mentioned first and second I/O ports 60, 62. The ablation signal generation circuit 66 may be configured to generate and output an RF signal having signal characteristics appropriate for performing an ablation procedure on tissue of a patient such as, for example, the heart. The ablation signal generation circuit 66 may be electrically coupled with the first I/O port 60 for outputting the ablation signal through the ablation catheter I/O cable 56 to the ablation catheter. In an embodiment, the ablation signal may have a frequency of between four hundred and fifty (450) kilohertz (kHz) and five hundred (500) kHz, for example. Still further, the ablation signal may have a frequency of about four hundred and eighty-five (485) kHz, for example. Of course, other ablation signal frequencies may be generated in addition to or instead of a 450-500 kHz signal.

The filtering circuit 68 may be disposed between the first port 60 (i.e., the electrogram input node) and the second port 62 (i.e., the electrogram output node), in an embodiment. More broadly, the filtering circuit 68 may be electrically disposed in the electrogram signal path. Accordingly, the illustrated embodiment, in which the filtering circuit 68 is included in the ablation generator 20, is exemplary in nature only. Referring to FIGS. 1 and 4, the filtering circuit 68, or portions thereof, may additionally or alternatively be provided in the a tissue contact and coupling monitor 22, in the record and data consolidation system 18, in the EP recording system 14, or in another system or apparatus or in independent hardware, in embodiments.

The filtering circuit 68 may include, in an embodiment, one or more filter channels. The filtering circuit 68 may include the same number of channels as the number of electrodes on the ablation catheter, in an embodiment. For example, referring to FIGS. 2 and 4, in an embodiment in which the filtering circuit is configured to function with the illustrated embodiment of the ablation catheter 28, the filtering circuit may include four (4) channels. Of course, more or fewer channels may be provided, in an embodiment. One dedicated channel may be provided in the filtering circuit 68 for each electrode on the ablation catheter. The channels may be in parallel, in an embodiment.

Figure 5:
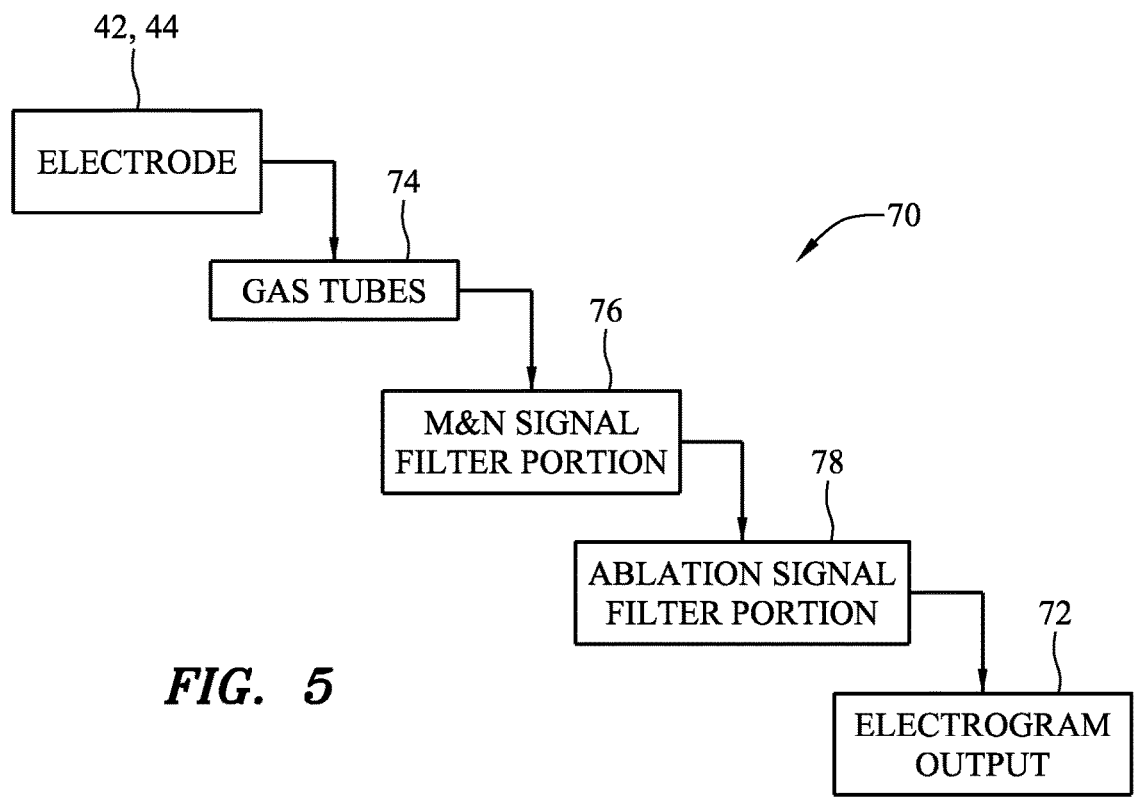
FIG. 5 is a block diagram view of an exemplary embodiment of a channel of a filtering circuit that may find use in the electrophysiology system of FIG. 1.

FIG. 5 is a diagrammatic view of an exemplary embodiment of a channel 70 of the filtering circuit, illustrating the signal path from an electrode 42, 44 (e.g., on the ablation catheter) to an electrogram output 72 (e.g., the second port 62 of the ablation generator, see FIG. 4). The filtering circuit channel 70 may include a gas tube discharge portion 74, a mapping and navigation signal filter portion 76, and an ablation signal filter portion 78. The channel 70 may be provided between an electrogram input node and an electrogram output node.

The mapping and navigation signal filter portion 76 may be provided to present a high impedance (e.g., ten (10) kilo-ohms (kΩ) or more) to signals having a frequency of or near the frequencies used by the mapping and navigation system 16 (see FIGS. 1 and 12) such as, for example, the signals driven through the patient's body for position determination purposes. Because the impedance in the signal path including the mapping and navigation signal filter portion 76 (i.e., through the filter channel 70) may be significantly higher than the impedance through the patient's body and the impedance presented by the signal path provided between electrodes 42, 44 and the mapping and navigation system, the position determination signals will not be diverted (or will be minimally diverted) through the electrogram signal path.

The ablation signal filter portion 78 may be provided to present a high impedance (e.g., ten (10) kΩ or more) to signals having a frequency of or near the frequencies used by the ablation generator 20 (see FIGS. 1 and 4) such as, for example, the signal driven through the ablation catheter and RF indifferent patch for ablating tissue. Because the impedance in the signal path including the ablation signal filter portion may be significantly higher than the impedance through the patient's body, ablation signals will not be diverted (or will be minimally diverted) through the electrogram signal path from its intended signal path. As a result, other components and equipment may be protected from high ablation currents, and the patient may be protected from ablation currents flowing between electrodes on the ablation catheter (i.e., using a first electrode on the ablation catheter as a source and a second electrode on the catheter as a sink), rather than between a single electrode and an RF indifferent patch.

Figure 6:
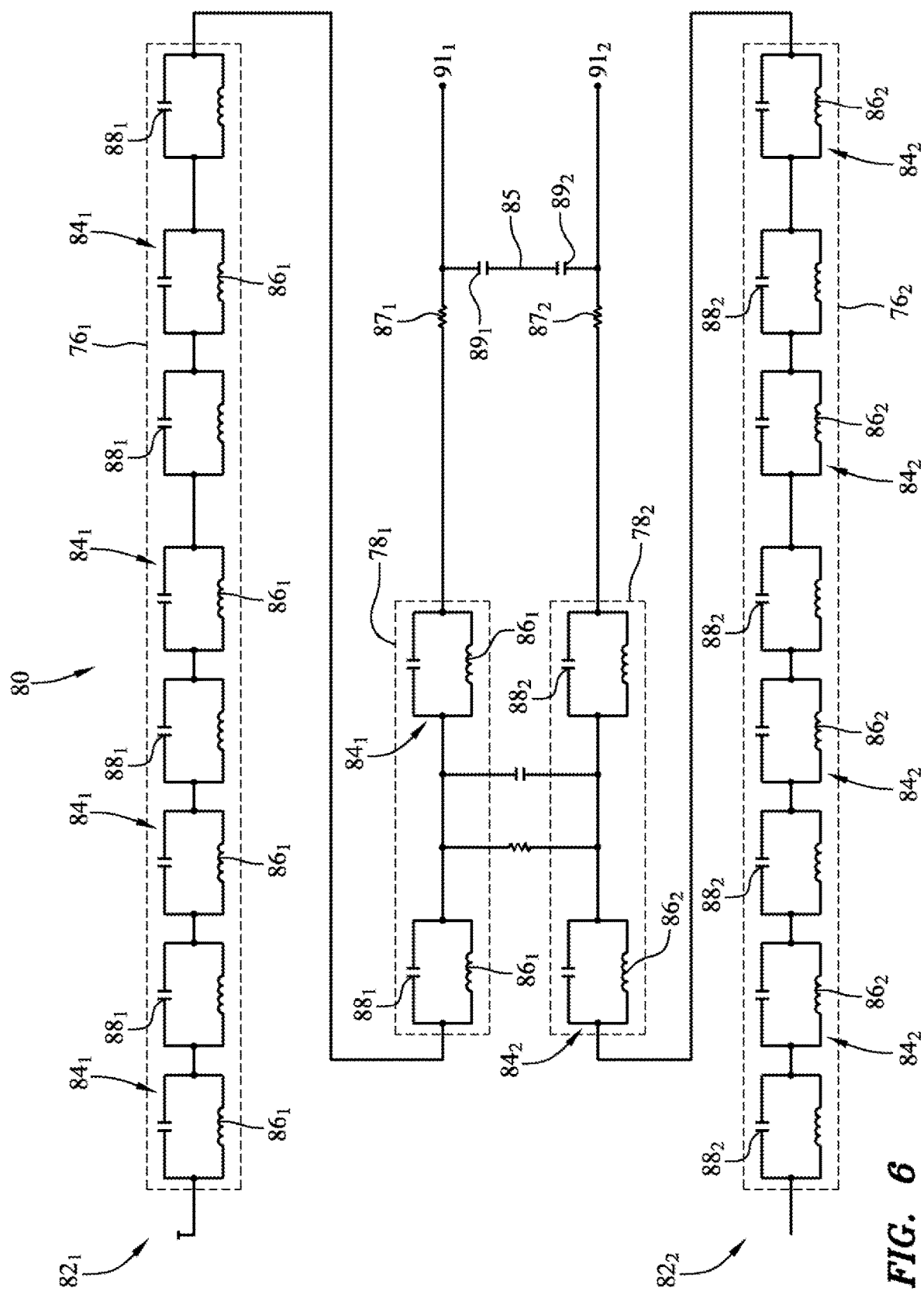
FIG. 6 is a schematic view of an exemplary embodiment of two channels of a filtering circuit that may find use in the electrophysiology system of FIG. 1, for example.

FIG. 6 is a schematic view of an exemplary two-channel embodiment 80 of the filtering circuit. The two channels $82_1$, $82_2$ may be identical, in an embodiment, as illustrated in FIG. 6. Accordingly, a single channel 82 is described below, but it should be understood that such description may apply to a respective channel 82 for each electrode on an ablation catheter, in an embodiment. Identical or similar components in the channels 82 are designated with a subscript "1" in the first channel and a subscript "2" in the second channel in FIG. 6, but are described generically without subscripts.

A channel 82 may include a mapping and navigation signal filter portion 76 and an ablation signal filter portion 78 (the gas discharge tubes shown in FIG. 5 are omitted in FIG. 6). The mapping and navigation filter signal portion 76 and ablation signal filter portion 78 may each comprise a respective one or more LC traps 84, in an embodiment. Accordingly, the channel may include a plurality of LC traps 84 (for clarity of illustration, not all LC traps 84 are designated in FIG. 6). Each LC trap 84 may include an inductor 86 in parallel with a capacitor 88 (for clarity of illustration, not all inductors 86 and capacitors 88 are designated in FIG. 6). The LC traps 84 may be electrically connected to each other in series, in an embodiment. The mapping and navigation signal filter portion 76 may include three (3) or more LC traps 84, in an embodiment. Eight (8) LC traps 84 are included in the embodiment of the mapping and navigation signal filter portion 76 illustrated in FIG. 6. The ablation signal filter portion 78 may include two or more LC traps 84, in an embodiment. A channel 82 and/or a node between two or more channels $82_1$, $82_2$, may additionally include other capacitors, inductors, resistors, and other electrical components for inputting, outputting, amplifying, and conditioning signals, and the like.

Each of the LC traps 84 may be tuned to a different peak frequency, in an embodiment (i.e., where the impedance of a given LC trap 84 is highest at its peak frequency). The peak frequency f (in hertz) of an LC trap is defined by equation 1, below:

$$f = \frac{1}{2\pi\sqrt{LC}} \quad (1)$$

where L is the inductance value of the inductor (in Henry) and C is the capacitance value of the capacitor (in farads). Accordingly, the LC traps 84 may differ from each other in inductance, capacitance, or both capacitance and inductance so as to be tuned to different peak frequencies. Alternatively, two or more of the LC traps 84 may be tuned to the same frequency, in an embodiment.

In an embodiment, the LC traps 84 in the mapping and navigation signal filter portion 76 may be tuned to respective peak frequencies at or near one or more frequencies used by a mapping and navigation system 16 (see FIG. 1) or of the same order of magnitude of such frequencies. For example, in an embodiment in which the mapping and navigation system 16 uses signals having a frequency of or near 8.138 kHz, for example, one or more of the LC traps 84 in the mapping and navigation signal filter portion 76 may be tuned to respective peak frequencies at or around 8.138 kHz. For example, one or more of the LC traps 84 in the mapping and navigation signal filter portion 76 (e.g., all of the LC traps 84 in the mapping and navigation signal filter portion 76) may be tuned to respective peak frequencies between about 6 kHz and about 8 kHz. Further, one or more of the LC traps 84 in the mapping and navigation signal filter portion 76 may be tuned to a respective frequency between about 6 kHz and about 7 kHz.

In an embodiment, one or more of the LC traps 84 in the ablation signal filter portion 78 may be tuned to respective peak frequencies at or near one or more frequencies used by an ablation generator 20 (see FIGS. 1 and 4) or the harmonics of such frequencies, such as second order and higher harmonics, or of the same order of magnitude of such frequencies and harmonics. For example, in an embodiment in which the ablation generator produces ablation signals having a frequency of 485 kHz, for example, one or more of the LC traps 84 in the ablation signal filter portion 78 may be tuned to respective peak frequencies at or around 485 kHz and/or a harmonic of 485 kHz. For example, one of the LC traps 84 in the ablation signal filter portion 78 may be tuned to a peak frequency of 485 kHz, and another LC trap 84 in the ablation signal filter portion 78 may be tuned to a harmonic of 485 kHz, such as the third harmonic of 485 kHz (at 1.455 MHz), for example only.

By presenting a high impedance to signals having frequencies at or near the peak frequencies of the LC traps 84, a filtering circuit according to the present disclosure may discourage the flow of such signals through the filtering circuit. Accordingly, by placing the filtering circuit in the electrogram signal path and tuning the peak frequencies of the LC traps 84 to frequencies at or near the frequencies of position determination signals, ablation signals, and other signals, such position determination signals, ablation signals, and other signals may be effectively prevented from being diverted through the electrogram signal path.

In an embodiment, additional filtering of the ablation signal in each channel may be provided by a resistor-capacitor (RC) filter comprising a resistor 87 and a capacitor 89. The resistor may have a relatively low impedance value, on the order of 25 ohms, in an embodiment, so as not to interfere with pacing. The capacitor 89 may be large enough that the RC filter is centered at a frequency below the fundamental ablation frequency, but not so large as to shunt the electrogram signal or the navigation signal. For example, a value on the order of 33 nanofarads may be appropriate, in an embodiment. A node 85 that couples the capacitors $89_1$, $89_2$, together may additionally couple similarly-placed capacitors in embodiments with additional channels. Output from the channels may be provided at output nodes $91_1$, $91_2$.

Although the filtering circuit is described above with respect to an embodiment having two substantially identical channels, it should be understood that different channels may differ, in an embodiment, so as to provide different types of filtering (e.g., different impedances and/or different frequencies) in different channels. For example, in an embodiment, the filtering circuit may be configured to function with a four-electrode catheter having a tip electrode and three ring electrodes (see FIG. 2). In practice, a physician may typically use such a catheter to view bipolar electrograms collected with adjacent electrode pairs, such as the tip electrode with the first ring electrode and the second ring electrode with the third ring electrode. Accordingly, in such an embodiment, the filtering circuit may be configured to filter substantially equally between the tip electrode and the first ring electrode and between the second and third ring electrodes, but to minimally filter between the first ring electrode and the second ring electrode, which may not commonly be used in a bipolar pair. Respective configurations of embodiments of the filtering circuit may be similarly tailored to common uses of medical devices with which those filtering circuit embodiments are used.

Although the filtering circuit is described herein with specific reference to filtering position determination signals from a mapping and navigation system and ablation signals, a filtering circuit according to the present disclosure may include filter portions for additional or alternative signals. That is, a filtering circuit is not limited to filtering a particular frequency or set of frequencies except as expressly set forth in the claims.

Figure 7:
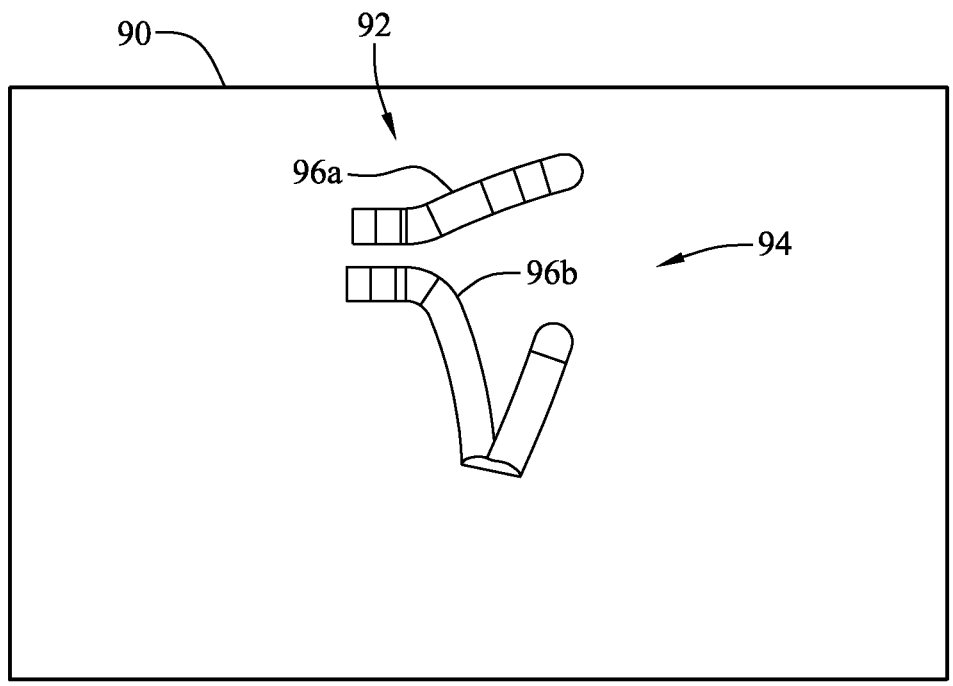
FIG. 7 illustrates position determinations of a mapping and navigation system in a system without a filtering circuit according to an embodiment of the present disclosure.
Figure 8:
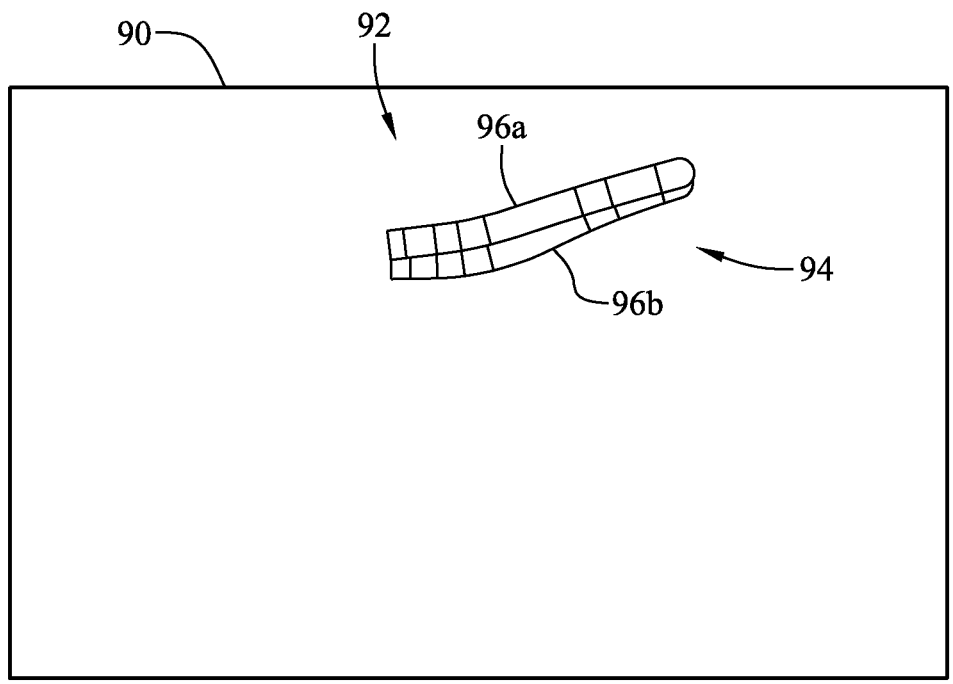
FIG. 8 illustrates position determinations of a mapping and navigation system in a system with a filtering circuit according to an embodiment of the present disclosure.
Figure 9A:
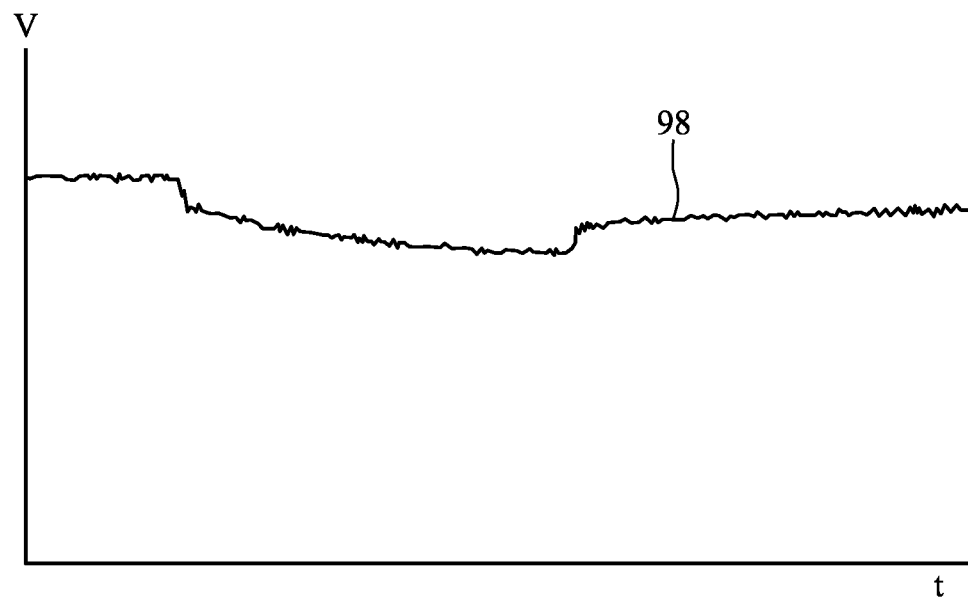
FIGS. 9A-10B are plots illustrating exemplary pacing functionality of an EP stimulator and ablation generator.
Figure 9B:
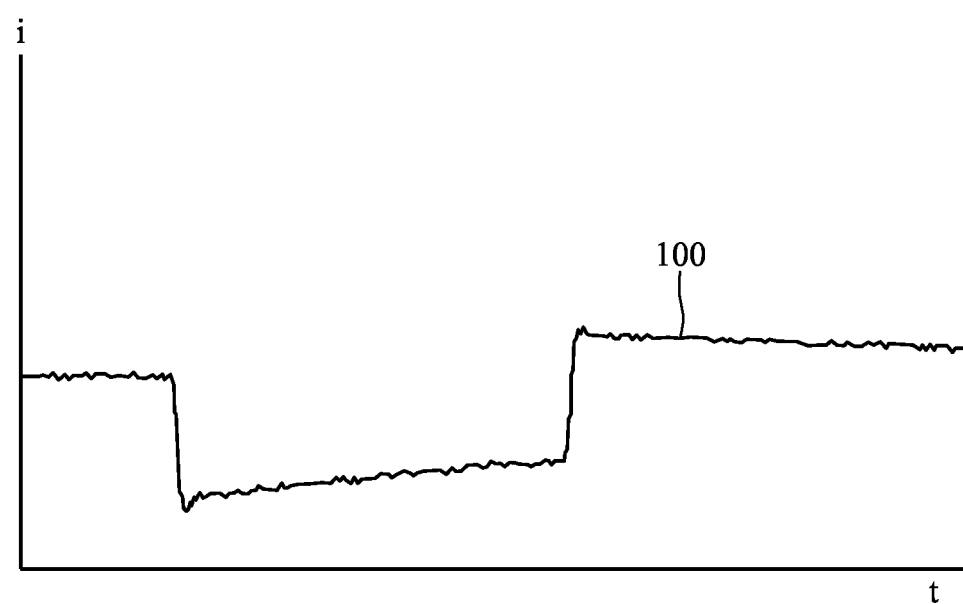

FIGS. 7-9 are diagrammatic views of a display 90 and user interface 92 that may find use in an EP system, illustrating electrode position and catheter shape determinations with and without a filtering circuit. FIG. 7 illustrates a catheter representation based on position determinations of a mapping and navigation system in a broader system lacking a circuit for filtering position determination frequencies from an electrogram (i.e., such that position determination signals are diverted through an electrogram signal path). FIG. 8 illustrates catheter representations based on position determinations of a mapping and navigation system in a broader system having a circuit for filtering position determination frequencies from an electrogram.

FIG. 7 illustrates a display 90 and user interface 92 that may be a part of, for example only, a mapping and navigation system. As described herein, the mapping and navigation system may determine the positions of one or more electrodes within the patient's body according to electrical signals detected with the electrodes that are transmitted by cutaneous patch electrodes, in an embodiment. FIG. 7 includes illustrations of a distal end portion 94 of an elongate medical device with the distal end portion deflected. A first illustration 96a of the elongate medical device 94 represents the "true" shape of the distal end portion. A second illustration 96b of the elongate medical device represents the shape of the distal end portion as determined by a mapping and navigation system used in an EP system without a filtering circuit according to the present disclosure. Accordingly, position determination signals of the mapping and navigation system are diverted through the electrogram signal path, and position determinations are skewed such that the determined positions of the tip electrode and first ring electrode result in a distorted reconstruction of the shape of the distal end portion of the elongate medical device in the second illustration 96b.

FIG. 8 illustrates the display 90 and user interface 92, including representations of the distal end portion of the elongate medical device 94 with the distal end portion deflected. A first illustration 96a of the elongate medical device represents the "true" shape of the distal end portion, and second and third illustrations 96b, 96c of the elongate medical device represents the shape of the distal end portion as determined by a mapping and navigation system used in an EP system with a filtering circuit according to the present disclosure. As can be seen comparing FIG. 8 with FIG. 7, by using a filtering circuit according to the present disclosure, position determinations made by a mapping and navigation system may be more accurate.

Figure 10A:
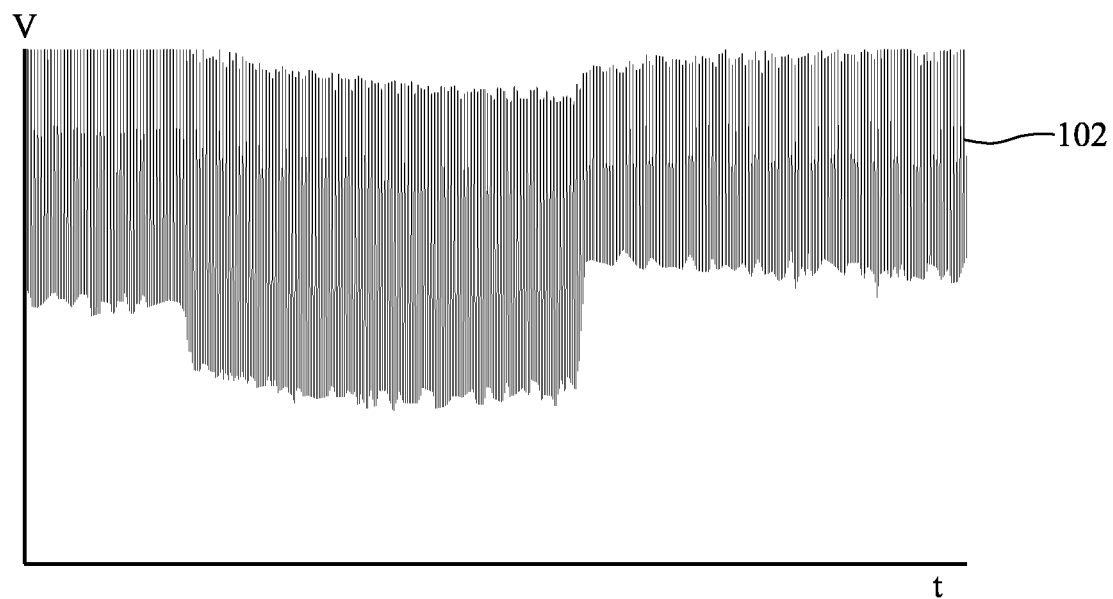
Figure 10B:
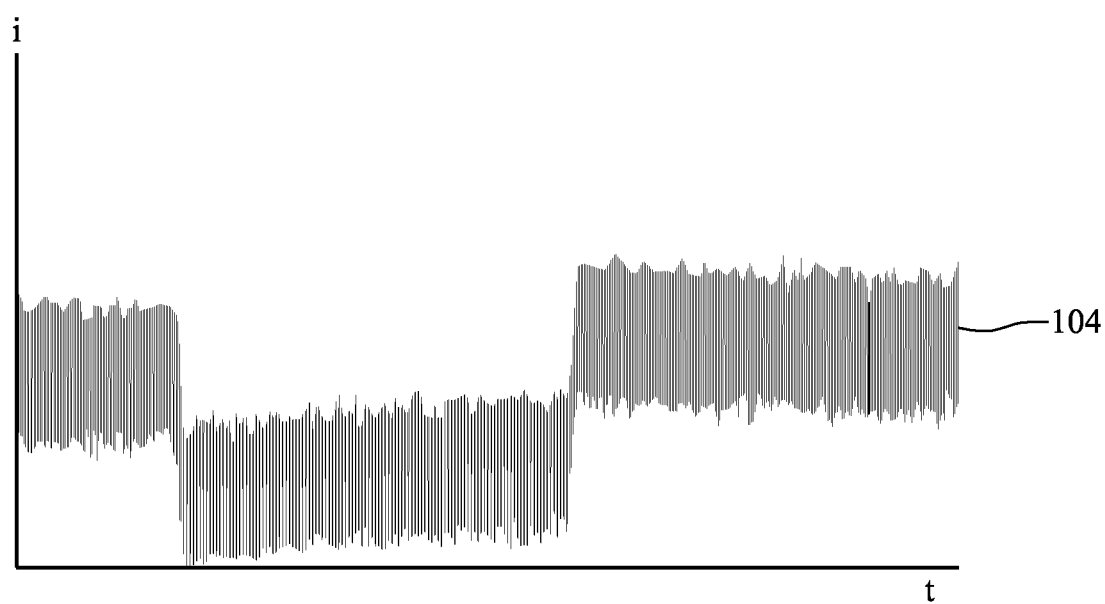

Pacing Functionality. While preventing leakage of position determination signals from a mapping and navigation system and return of ablation signals, a filtering circuit according to the present disclosure may provide relatively low impedance for pacing signals (e.g., provided by an EP stimulator 12, see FIG. 1), in an embodiment, permitting pacing signals to be driven through an ablation catheter in addition to or instead of an ablation signal. FIGS. 9 and 10 are plots illustrating a ten (10) millisecond (ms) pacing pulse being driven through an ablation catheter, measured between a tip electrode and first ring electrode (e.g., tip electrode 44 and adjacent ring electrode 42, see FIG. 2). FIG. 9 illustrates an exemplary pacing pulse as generated by an EP stimulator, with a first representation 98 in FIG. 9 illustrating the voltage of the pulse (where a voltage of the pulse may be about two volts, in an exemplary embodiment), and a second representation 100 in FIG. 9 representing the current of the pulse (where a current of the pulse may be about four milliamps, in an exemplary embodiment). FIG. 10 illustrates the same exemplary pacing pulse in the presence of a small ablation voltage used for monitoring, with a first representation 102 in FIG. 10 illustrating the voltage between the tip electrode and the first ring electrode, and a second representation 104 in FIG. 10 representing the current of the tip electrode to the first ring electrode. As illustrated, the pacing signal produced by the EP stimulation system is substantially transmitted by the ablation catheter electrode and "rides" on the ablation signal.

Figure 11:
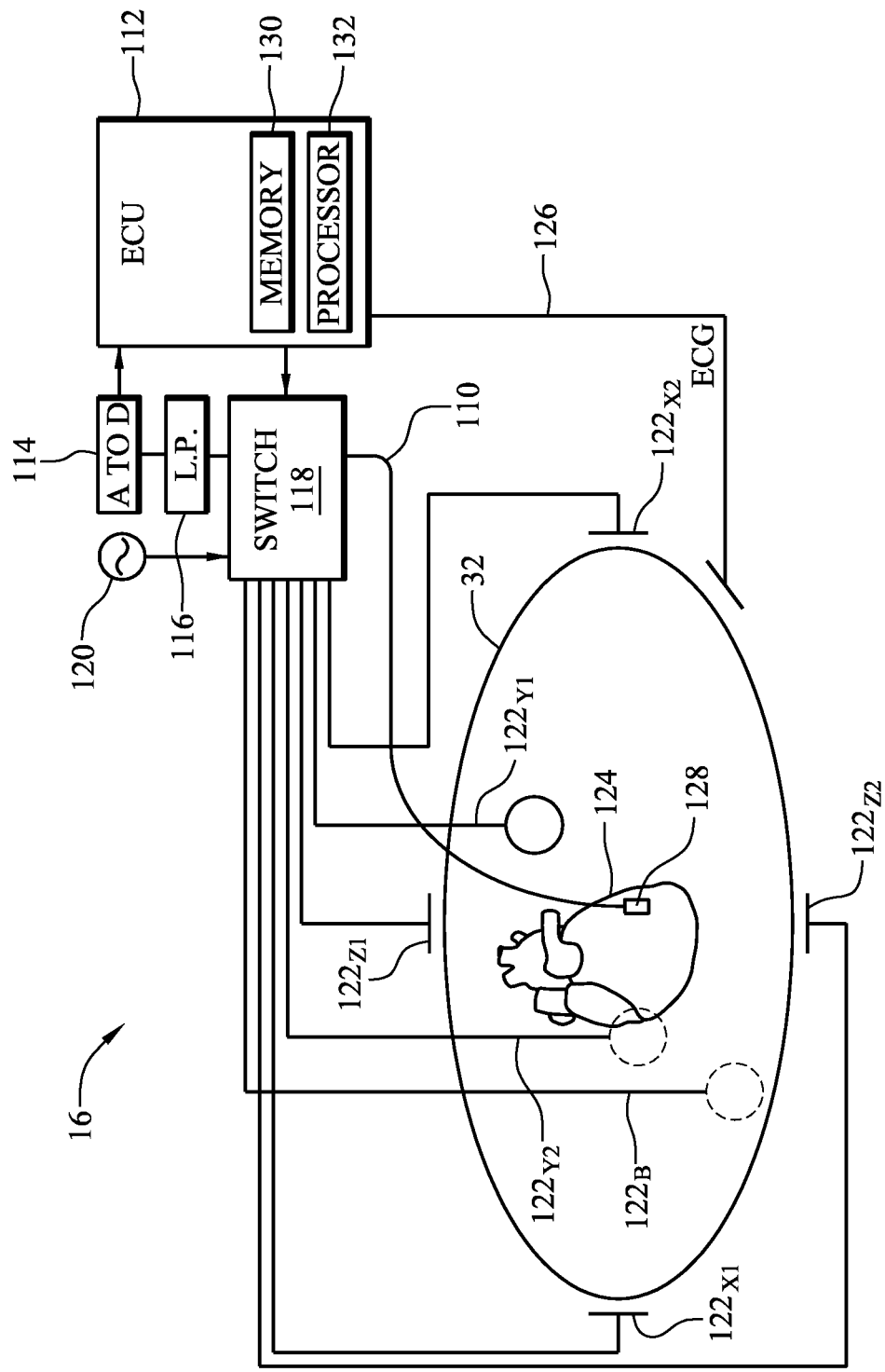
FIG. 11 is a diagrammatic depiction of an exemplary embodiment of a mapping and navigation system.

Exemplary Mapping and Navigation System. FIG. 11 is a diagrammatic depiction of an embodiment of an exemplary mapping and navigation system 16 that may incorporate various functionality including, but not limited to, determining the location (i.e., position and orientation) of an elongate medical device 110 within the body of a patient 32, mapping the anatomy of the patient 32, etc.

The system 16 may include an electronic control unit (ECU) 112, an analog-to-digital converter (A-to-D) 114, a lowpass filter (L.P.) 116, a switch 118, a signal generator 120, and a plurality of body surface (i.e., cutaneous) patch electrodes 122. The system 16 may be electronically and/or mechanically coupled with an elongate medical device 110. The system may be configured for a number of functions for guiding the elongate medical device 110 to a target site within the body of a patient 32, such as the heart 124, and for assessing contact between the elongate medical device 110 and the tissue of the patient 32. The system 16 may further include a conventional set of ECG leads 126 for the capture and measurement of patient ECG data.

The elongate medical device 110 may be one of the catheters 24, 26, 28 described herein (see FIGS. 1-3), or some other elongate medical device. The elongate medical device 110 may have one or more electrodes 128. The one or more electrodes may include a tip electrode 44 (see FIG. 2), one or more ring electrodes 42 (see FIG. 2), and/or another type of electrode.

The ECU 112 may include a memory 130 and a processor 132. The memory 130 may be configured to store data respective of the elongate medical device 110, of the patient 32, and/or other data. Such data may be known before a medical procedure, or may be determined and stored during a procedure. The memory 130 may also be configured to store instructions that, when executed by the processor 132, cause the ECU 112 to perform one or more methods, steps, functions, or algorithms described herein.

The system may be configured to determine the position and orientation (P&O) of the elongate medical device 110 (e.g., of a distal end portion of the elongate medical device 110) within the body of the patient 32. Accordingly, the ECU 112 may be configured to control generation of one or more electrical fields and determine the position of one or more electrodes 128 within those fields. The ECU 112 may thus be configured to control the signal generator 120 in accordance with predetermined strategies to selectively energize various pairs (dipoles) of body surface patch electrodes 122 and catheter electrodes 128.

The body surface patch electrodes 122 may be used to generate axes-specific electric fields within the body of the patient, and more specifically within the heart 124, in an embodiment. Three sets of patch electrodes may be provided: (1) electrodes $122_{X1}$, $122_{X2}$ (X-axis); (2) electrodes $122_{Y1}$, $122_{Y2}$ (Y-axis); and (3) electrodes $122_{Z1}$, $122_{Z2}$ (Z-axis). Additionally, a body surface electrode ("belly patch") $122_B$ may be provided as an electrical reference. The body patch electrodes $122_{X1}$, $122_{X2}$, $122_{Y1}$, $122_{Y2}$, $122_{Z1}$, $122_{Z2}$, $122_B$ may be referred to herein generically as a body patch electrode 122 or as the body patch electrodes 122. Body patch electrode configurations and combinations other than those explicitly illustrated and described are suitable for use with the present disclosure, including fewer body patch electrodes 122, more body patch electrodes 122, or different physical arrangements, e.g. a linear arrangement instead of an orthogonal arrangement.

Each patch electrode 122 may be independently coupled to the switch 118, and pairs of patch electrodes may be selected by software running on the ECU 112 to couple the patch electrodes 122 to the signal generator 120. A pair of electrodes 122, for example the Z-axis electrodes $122_{Z1}$, $122_{Z2}$, may be excited by the signal generator 120 to generate an electrical field in the body of the patient 32 and, more particularly, within the heart 124, by driving a current between the excited electrodes. Such driven currents are referred to above as positioning determination signals.

In an embodiment, this electrode excitation process occurs rapidly and sequentially as different sets of patch electrodes 122 are selected and one or more of the unexcited surface electrodes 122 are used to measure voltages. During the delivery of the excitation signal (e.g., current pulse), the remaining (unexcited) patch electrodes 122 may be referenced to the belly patch $122_B$ and the voltages impressed on these remaining electrodes 122 may be measured. In this fashion, the patch electrodes 122 may be divided into driven and non-driven electrode sets. The low pass filter 116 may process the voltage measurements. The filtered voltage measurements may be transformed to digital data by the analog to digital converter 114 and transmitted to the ECU 112 for storage (e.g. in the memory 130) under the direction of software. This collection of voltage measurements may be referred to herein as the "patch data." The software may store and have access to each individual voltage measurement made at each surface electrode 122 during each excitation of each pair of surface electrodes 122.

Generally, in an embodiment, three nominally orthogonal electric fields may be generated by the series of driven and sensed electric dipoles in order to determine the location of the elongate medical device 110 (i.e., of one or more electrodes 128). Alternately, these orthogonal fields can be decomposed and any pair of surface electrodes 122 (e.g., non-orthogonal) may be driven as dipoles to provide effective electrode triangulation.

The patch data may be used, along with measurements made at one or more electrodes 128 and measurements made at other electrodes and devices, to determine a relative location of the one or more electrodes 128. In some embodiments, electric potentials across each of the six orthogonal patch electrodes 122 may be acquired for all samples except when a particular surface electrode pair is driven. In an embodiment, sampling electric potentials may occur at all patch electrodes 122, even those being driven.

As a part of determining locations of various electrodes 128, the ECU 112 may be configured to perform one or more compensation and adjustment functions, such as motion compensation. Motion compensation may include, for example, compensation for respiration-induced patient body movement, as described in U.S. patent application publication no. 2012/0172702, which is hereby incorporated by reference in its entirety.

Data sets from each of the patch electrodes 122 and the electrodes 128 are all used to determine the location of the electrodes 128 within the patient 32. After the voltage measurements are made for a particular set of driven patch electrodes 122, a different pair of patch electrodes 122 may be excited by the signal generator 120 and the voltage measurement process of the remaining patch electrodes 122 and electrodes 122 takes place. The sequence may occur rapidly, e.g., on the order of 100 times per second in an embodiment. The voltage on the electrodes 128 within the patient may bear a linear relationship with the position of the electrodes 128 between the patch electrodes 122 that establish the electrical fields, as more fully described in U.S. Pat. No. 7,263,397 referred to above.

In summary, FIG. 11 shows an exemplary mapping and navigation system 16 that employs seven body patch electrodes 122, which may be used for injecting current and sensing resultant voltages. Current may be driven between two patches 122 at any time. Positioning measurements may be performed between a non-driven patch 122 and, for example, belly patch $122_B$ as a ground reference. An electrode bio-impedance may be computed according to the following equation (2):

$$BioZ[n \to m][k] = \frac{V_k}{I_{n \to m}} \quad (2)$$

where $V_k$ is the voltage measured on electrode k and $I_{n \to m}$, is a known constant current driven between electrodes n and m. The position of an electrode 128 may be determined by driving current between different sets of patches 122 and measuring one or more impedances. In one embodiment, time division multiplexing may be used to drive and measure all quantities of interest. Position determining procedures are described in more detail in, for example, U.S. Pat. No. 7,263,397 and publication no. 2007/0060833 referred to above.

In addition to a simple impedance, the systems and methods described herein may be used to determine a complex impedance respective of one or more electrodes on a catheter. Such complex impedances may be used to assess a contact state between an electrode and tissue. For example, as described in U.S. Pat. No. 8,403,925, which is hereby incorporated by reference in its entirety, a complex impedance may be used to determine an electrical coupling index (ECI), which in turn may be used to assess contact between an electrode and tissue. Such complex impedance, ECI, and related calculations and related contact state determinations may be made by the tissue contact and coupling monitor shown in FIG. 1.

Although numerous embodiments of this invention have been described above with a certain degree of particularity, those skilled in the art could make numerous alterations to the disclosed embodiments without departing from the spirit or scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims. Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ablation generator comprising:
   a circuit for generating an RF ablation signal having a frequency appropriate for performing an ablation procedure on tissue of a patient;
   an input port for receiving a monitoring signal respective of the tissue of the patient;
   an output port for providing the monitoring signal to another device; and
   a filtering circuit disposed between the input port and the output port;
   wherein said filtering circuit is configured to present a high impedance at a frequency at or near which a mapping and navigation system associated with the ablation generator transmits a signal;
   wherein said filtering circuit comprises two channels, each channel comprising a first and a second filter portion, each comprising a respective plurality of LC traps, each LC trap comprising an inductor in parallel with a capacitor, the LC traps being placed in series; and
   wherein a first plurality of the LC traps in said first filter portion are tuned to a first same peak frequency between six kilohertz and eight kilohertz, and a second plurality of said LC traps of the first filter portion are tuned to a second same peak frequency between six kilohertz and about seven kilohertz.

2. The ablation generator of claim 1, wherein said input port comprises respective channels for a plurality of electrodes on a medical device.

3. The ablation generator of claim 1, wherein the plurality of LC traps of the second filter portion are tuned to or near a harmonic of said frequency of said RF ablation signal.

* * * * *